US010155943B2

(12) United States Patent
Fox

(10) Patent No.: US 10,155,943 B2
(45) Date of Patent: *Dec. 18, 2018

(54) METHOD OF GENERATING AN OPTIMIZED, DIVERSE POPULATION OF VARIANTS

(71) Applicant: Codexis, Inc., Redwood City, CA (US)

(72) Inventor: Richard Fox, Kirkwood, MO (US)

(73) Assignee: Codexis, Inc., Redwood City, CA (US)

( * ) Notice: Subject to any disclaimer, the term of this patent is extended or adjusted under 35 U.S.C. 154(b) by 1137 days.

This patent is subject to a terminal disclaimer.

(21) Appl. No.: 14/281,421

(22) Filed: May 19, 2014

(65) Prior Publication Data

US 2014/0256557 A1   Sep. 11, 2014

Related U.S. Application Data

(62) Division of application No. 12/867,433, filed as application No. PCT/US2009/033971 on Feb. 12, 2009, now Pat. No. 8,768,871.

(60) Provisional application No. 61/028,178, filed on Feb. 12, 2008.

(51) Int. Cl.
| *C12N 15/10* | (2006.01) |
| *C40B 50/02* | (2006.01) |
| *G06F 19/00* | (2018.01) |
| *G06N 3/12* | (2006.01) |
| *G06F 19/24* | (2011.01) |

(52) U.S. Cl.
CPC ..... *C12N 15/1089* (2013.01); *C12N 15/1058* (2013.01); *C40B 50/02* (2013.01); *G06N 3/126* (2013.01); *G06F 19/24* (2013.01); *G06F 19/707* (2013.01)

(58) Field of Classification Search
None
See application file for complete search history.

(56) References Cited

U.S. PATENT DOCUMENTS

| 5,605,793 | A | 2/1997 | Stemmer |
| 5,811,238 | A | 9/1998 | Stemmer et al. |
| 5,830,721 | A | 11/1998 | Stemmer et al. |
| 5,834,252 | A | 11/1998 | Stemmer et al. |
| 5,837,458 | A | 11/1998 | Minshull et al. |
| 6,117,679 | A | 9/2000 | Stemmer |
| 6,376,246 | B1 | 4/2002 | Crameri et al. |
| 6,586,182 | B1 | 7/2003 | Patten et al. |
| 7,603,326 | B2 | 10/2009 | Bonabeau et al. |
| 7,783,428 | B2 | 8/2010 | Gustafsson et al. |
| 8,768,871 | B2 | 7/2014 | Fox |
| 2006/0205003 | A1 | 9/2006 | Gustafsson et al. |
| 2007/0208677 | A1 | 9/2007 | Goldberg et al. |
| 2008/0220990 | A1 | 9/2008 | Fox |
| 2009/0118130 | A1 | 5/2009 | Mundorff et al. |
| 2009/0312196 | A1 | 12/2009 | Colbeck et al. |

FOREIGN PATENT DOCUMENTS

| EP | 1589463 | A1 | 10/2005 |
| WO | 95/22625 | A1 | 8/1995 |
| WO | 98/27230 | A1 | 6/1998 |
| WO | 99/29902 | A1 | 6/1999 |
| WO | 00/42560 | A2 | 7/2000 |
| WO | 00/42561 | A2 | 7/2000 |
| WO | 01/64864 | A2 | 9/2001 |
| WO | 01/75767 | A2 | 10/2001 |
| WO | 02/45012 | A2 | 6/2002 |

OTHER PUBLICATIONS

Altschul, S., et al., "Basic local alignment search tool," J. Mol. Biol., 215: 403-410, 1990.
Altschul, S., et al., "Gapped BLAST and PSI-BLAST: a new generation of protein database search programs," Nucleic Acids Res., 25(17):3389-3402, 1997.
Darwen, P., et al., "Speciation as automatic categorical modularization," IEEE Transactions on Evolutionary Computation, 1(2):101-108, 1997.
Darwen, P., et al., "Every niching method has its niche: fitness sharing and implicit sharing compared," Proc. of Parallel Problem Solving from Nature (PPSN) IV, Vol.1141, Lecture Notes in Computer Science, pp. 398-407,Springer-Verlag, 1996.
Deb, K., "Multiobjective genetic algorithms: problem difficulties and construction of test problems," Evolutionary Computation, 7(3):205-230, 1999.
Henikoff, S., et al., "Amino Acid Substitution Matrices from Protein Blocks", Proc. Natl. Acad. Sci. USA, 89:10915-19, 1992.
Horn, J., et al., "A niched pareto genetic algorithm for multiobjective optimization," In Proceedings of the First IEEE Conference on Evolutionary Computation, IEEE World Congress on Computational Computation, 1:82-87, 1994.
Kubo, T., et al., "Enantioselective epoxidation of terminal alkenes to (R)- and (S)-epoxides by engineered cytochromes P450 BM-3," Chemistry, 12(4):1216-20, 2006.
Landwehr, M., et al., "Diversification of catalytic function in a synthetic family of chimeric cytochrome p450s," Chem Biol, 14(3):269-78, 2007.
Needleman, S., et al., "A general method applicable to the search for similarities in the amino acid sequence of two proteins," J. Mol. Biol. 48:443-453, 1970.
Ness, J., et al., "Synthetic shuffling expands functional protein diversity by allowing amino acids to recombine independently," Nature Biotechnology, 20:1251-1255, 2002.
Pearson, W., et al., "Improved Tools for Biological Sequence Comparison," Proc. Natl. Acad. Sci. USA, 85:2444-2448, 1988.
Smith, T., et al., "Comparison of Biosequences," Adv. Appl. Math, 2:482-489, 1981.
Stemmer, W., "DNA Shuffling by Random Fragmentation and Reassembly: In vitro Recombination for Molecular Evolution," Proc. Natl. Acad. Sci. USA, 91:10747-10751, 1994.
Willet, P., et al., "Genetic algorithms in molecular recoginition and design," Evolutionaly Computation, IEEE World Congress on Computational Intelleigence, Proceedings of the First IEEE Conference, Orlando, FL., USA, pp. 82-87, Jun. 27-29, 1994.

*Primary Examiner* — Lori A. Clow
(74) *Attorney, Agent, or Firm* — Weaver Austin Villeneuve & Sampson LLP

(57) ABSTRACT

The disclosure relates to a method of generating a diverse set of variants to screen improved and novel properties within the variant population, a system for creating the diverse set of variants, and the variant peptides.

23 Claims, 1 Drawing Sheet

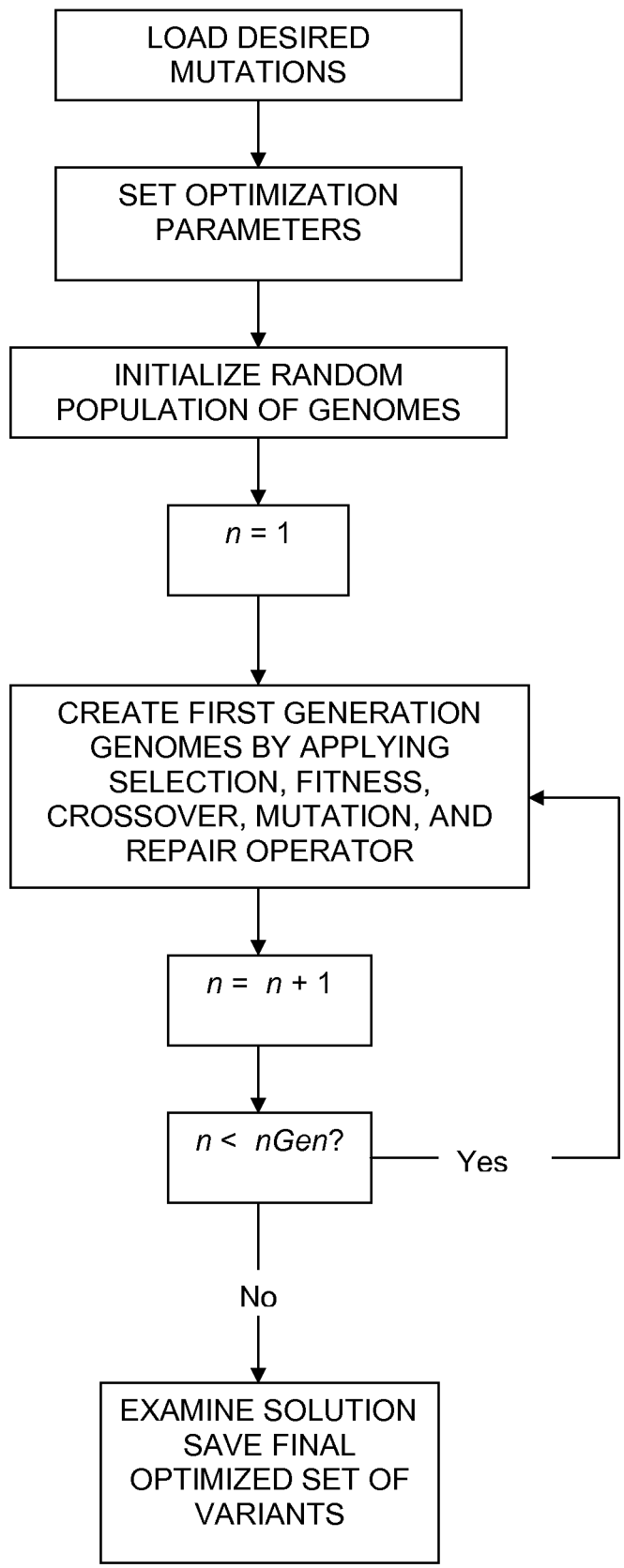

METHOD OF GENERATING AN OPTIMIZED, DIVERSE POPULATION OF VARIANTS

1. CROSS-REFERENCE TO RELATED APPLICATIONS

The present application is a Divisional of U.S. patent application Ser. No. 12/867,433, filed on Oct. 21, 2010, which claims priority to PCT/US2009/033971, filed on Feb. 12, 2009, which claims priority to U.S. Prov. Appln. Ser. No. 61/028,178, filed Feb. 12, 2008, all of which are hereby incorporated by reference in their entireties, for all purposes.

2. FIELD OF THE INVENTION

The present invention is directed to a method of creating an optimized, diverse population of sets of molecular variants, which can be used for identifying variants displaying altered or improved properties or novel activities. The method creates from a given set of defined variations in polypeptide or polynucleotide sequences (e.g., mutations) a diverse population of variants having maximal information content. The present disclosure further provides a computer-readable media, including program instructions, which when executed by a processor, create a set of molecular variants, a system for creating a set of molecular variants, a network based system for creating a set of variants, and the final synthesized set of molecular variants.

3. BACKGROUND OF THE INVENTION

Various techniques of in silico and in vitro based directed evolution of protein function have allowed the generation of proteins with novel properties. For example, cytochrome p450 enzymes have been evolved to have activity against substrates not normally recognized by the naturally occurring enzyme (see, e.g., Landwehr et al., 2007, *Chem Biol* 14(3):269-78; Kubo et al., 2006, *Chemistry* 12(4):1216-20). Increases in the efficiency of creating polypeptide variants allow the generation of large, diverse population sets that can be screened for improved or new activities. Targeted properties can include, among others, increased enzymatic activity, stereoselectivity, stereospecificity, thermal stability, inhibitor resistance, protease resistance, etc. Generally, selection of the variants for further evolution and screening is made following the testing of a set of mutated polypeptides for various desirable and/or undesirable properties, typically based on activity for a single substrate or ligand. This approach to variant selection, however, is not efficient, subject to human bias, and becomes more difficult as the number and complexity of the variants (e.g., population size) increases, and where a population of variants having different properties, e.g., activities against structurally different substrates or ligands, is being sought. Hence, it is beneficial to have methods for creating variants for purposes of testing and evolution of novel biological properties that can manage large sample sizes and diverse sets of performance criteria.

4. SUMMARY OF THE INVENTION

The present disclosure relates to a method of creating an optimized, diverse population of molecular variants, such as variant biologically active polypeptides. The method comprises the steps of:
  (a) inputting a desired set of mutations;
  (b) setting optimization parameters, wherein the optimization parameters comprise:
    (i) number, nvar, of molecular variants to create;
    (ii) molecular variant population size popSize;
    (iii) crossover probability crossrate;
    (iv) mutation rate, mutrate;
    (v) repair operator,
    (vi) primary fitness function;
    (vii) penalty fitness function; and
  (c) generating a random plurality of genomes of the population size popSize; and
  (d) creating a first generation of genomes of the size nvar by applying a selection operator, a crossover operator, a mutation operator, a repair operator, a primary fitness operator, and penalty function operator on the plurality of random genomes.

In some embodiments the method comprises the steps of:
  (a) inputting a desired set of mutations, wherein each mutation has associated with it a preferred frequency of appearance within the set of molecular variants and a weight;
  (b) setting optimization parameters, wherein the optimization parameters comprise:
    (i) number nvar of molecular variants to create;
    (ii) molecular variant population size popSize;
    (iii) crossover probability crossrate;
    (iv) mutation rate mutrate;
    (v) repair operator parameters: the minimum, maximum and desired number of mutations per molecular variant;
    (vi) number of generations to evolve nGen;
    (vii) setting the primary fitness function; and
    (viii) setting penalty fitness functions;
  (c) generating a random plurality of sets of molecular variants of the population size popSize, wherein each set of molecular variants is of size nvar; and
  (d) evolving new populations of sets of molecular variants for nGen generations by applying a selection operator, a crossover operator, a mutation operator, a repair operator, a primary fitness operator, and penalty function operator, wherein new populations are created by repeating the following steps:
    (i) selecting sets of molecular variants for breeding based on the selection operator; and
    (ii) breeding sets of molecular variants by;
      (aa) mating the molecular variants using the crossover operator; and
      (bb) mutagenizing progeny sets of molecular variants according to the mutation operator.

In some embodiments, the method further comprises the step of synthesizing the final set of molecular variants. In some embodiments, the method further comprises the step of testing the properties of the final set of molecular variants.

In some embodiments, the primary fitness function can comprise niche counting, D-optimality or A-optimality. The penalty fitness function can be a weighted penalty for the average number of mutations per genome or a weighted penalty for the occurrence of specified mutations.

The present disclosure further provides a computer program comprising a machine readable medium containing the program instructions, such as logic codes, for carrying out the steps of the methods herein. The software for carrying out the steps can be constructed by one of skill using a standard programming language such as Visual Basic, FORTRAN, Basic, Java, or the like.

Further provided are systems for carrying out the methods, where the systems comprise at least one computer comprising a database capable of storing the data set for a list of desired mutations, and system software for carrying out each of the steps of the methods above. The system can be part of a stand-alone computer manipulated by a user, or the system can be part of an internet based system, where a server provides the system software for carrying out one or more steps of the method and the client provides user definable information, such as the list of desired mutations, and values for the various optimization parameters.

In some embodiments, the present methods for creating an optimized diverse population of molecular variants find uses in creating variant polypeptides for testing of improved properties or novel activities (e.g., enzymatic activity), such as activity against a ligand or substrate not normally recognized by the naturally occurring polypeptides. The method can be used in conjunction with other methods of selecting a variant subset for the purposes of identifying an optimized, maximally diverse subset for further mutagenesis and testing of molecular activities.

In some embodiments, the present disclosure provides sets or libraries of molecular variants, such sets containing a diverse set of molecular variants that provides a high degree of information content. The mutations are created such that there is a high probability of creating new molecular variants with improved and/or novel properties. The sets of molecular variants created by the invention can be synthesized by traditional synthetic methods or by synthesis robots.

5. BRIEF DESCRIPTION OF THE FIGURES

FIG. 1 provides the flow diagram of the method of creating an optimized, diverse set of molecular variants.

6. DETAILED DESCRIPTION OF THE INVENTION

The present disclosure provides a method of creating an optimized, diverse population of sets of molecular variants, which can be used for identifying variants displaying altered properties or novel activities. The method creates from a given set of defined variations (e.g., mutations) a diverse population of molecular variants having maximal information content. The present disclosure further provides a computer-readable media including program instructions which when executed by a processor, create a set of molecular variants, a system for creating a set of molecular variants, a network-based system for creating a set of variants, and the final synthesized set of molecular variants. For the detailed description of embodiments, the following shall apply:

As used in this specification and the appended claims, the singular forms "a", "an" and "the" include plural referents unless the context clearly indicates otherwise. Thus, for example, reference to "a polypeptide" includes more than one polypeptide, and reference to "a compound" refers to more than one compound.

In addition, the use of "or" means "and/or" unless stated otherwise. Similarly, "comprise," "comprises," "comprising," "include," "includes," and "including" are interchangeable and not intended to be limiting.

It is to be further understood that where descriptions of various embodiments use the term "comprising," those skilled in the art would understand that in some specific instances, an embodiment can be alternatively described using the language "consisting essentially of" or "consisting of."

It is to be understood that both the foregoing general description, including the drawings, and the following detailed description, are exemplary and explanatory only, and are not restrictive of this disclosure.

The section headings used herein are for organizational purposes only and not to be construed as limiting the subject matter described.

6.2 Definitions

"Average Mutation Rate" refers to the average desired number of mutations in each molecular variant.

"Average Mutation Rate Weight" refers to the weight that multiplies deviations from the average mutation rate. The weighted deviations are then used to penalize the overall fitness by adding the following term to the overall fitness:

$$A_p = -w \cdot \sum_{i=1}^{i=n} (m_i - \langle m \rangle)^2,$$

where $A_p$ is the penalty term, w the penalty weight, i the variant index, n the number of variants to create, $m_i$ the number of mutations in the variant i, and $\langle m \rangle$ is the desired average mutation rate.

"Bio-molecule" refers to a molecule that is generally found in a biological organism, and includes biological macromolecules that are typically polymeric in nature and composed of multiple subunits (i.e., "biopolymers"). Typical bio-molecules include, but are not limited to, molecules that share some structural features with naturally occurring polymers such as RNAs (formed from ribonucleotide subunits or analogs thereof), DNAs (formed from deoxyribonucleotide subunits or analogs thereof), and polypeptides (formed from amino acid subunits and analogs thereof). Bio-molecules also include, e.g., lipids, carbohydrates, or other organic molecules that can be made by one or more genetically encodable molecules (e.g., one or more enzymes or enzyme pathways) or the like. Bio-molecule also refers to synthetic RNAs, DNAs, and polypeptides that while not naturally occurring, are still capable of biological activity.

"Crossover operator" refers to an operator that determines which parental strand is passed onto the progeny genome during mating of two genomes. It begins with one of two parent genomes, and at every gene locus the crossover probability is calculated as the per genome crossover rate divided by the length of the genome. In some embodiments, "Crossover operator" refers to an operator that is used to determine which molecular variant is passed on to a progeny set of molecular variants, during the mating between two sets of molecular variants. The process begins with one of two parent sets of variants. For every molecular variant, the crossover probability is calculated as the per (set of variants) crossover rate divided by the length of the set of variants. If a uniform random number drawn from the [0,1] scale is less than this per molecular variant probability, then copying is switched to the other parental set of variants. The process continues until the entire progeny set of molecular variants is constructed.

"Data structure" refers to the organization and optionally associated device for the storage of information, typically multiple "pieces" of information. The data structure can be a simple recordation of the information (e.g., a list) or the data structure can contain additional information (e.g., annotations) regarding the information contained therein, can establish relationships between the various "members" (i.e., information "pieces") of the data structure, and can provide pointers or links to resources external to the data structure. The data structure can be intangible but is rendered tangible when stored or represented in a tangible medium (e.g., paper, computer readable medium, etc). The data structure can represent various information architectures including, but not limited to, simple lists, linked lists, indexed lists, data tables, indexes, hash indices, flat file databases, relational databases, local databases, distributed databases, thin client databases, and the like. In some embodiments, the data structure provides fields sufficient for the storage of one or more character strings. The data structure is optionally organized to permit alignment of the character strings and, optionally, to store information regarding the alignment and/or string similarities and/or string differences. The term "encoded character string" refers to a representation of a biological molecule that preserves desired sequence/structural information regarding that molecule. As noted throughout, non-sequence properties of bio-molecules can be stored in a data structure in a manner analogous to sequence based structures.

"Descriptor" refers to something that serves to describe or identify an item. For example, characters in a character string can be descriptors of amino acids in a polypeptide being represented by the character string. Descriptor can also refer to properties of items, such as the activity of an enzyme on a particular substrate, or the selectivity or solvent stability of a polypeptide.

"Fitness" refers to the fitness of each genome based on a fitness function, which is applied by a fitness operator. Every set of molecular variants has a fitness associated with it. The fitness is calculated by summing the penalized fitnesses of each variant in the set. The fitnesses are initially penalized by the degree to which there are nearby neighbors in the local hypervolume. In this way, optimal sets of molecular variants will consist of variants which are distributed in genotype space. Alternatively, D-optimality, A-optimality or other information based criteria could be used to construct a matrix of molecular variants that contain the maximum information content for an objective property, such as activity, selectivity, etc., as a function of predictors (mutations).

"Gene" refers to a binary digit representing the presence or absence of a given variant within a genome. In some embodiments, "gene" refers to a string of binary digits that represent the presence or absence of a given mutation within a biomolecule sequence. The biomolecule sequence can be that of a polypeptide, a polynucleotide, or any other polymeric biological molecule. Genes are initially created by randomly assigning bits from a pool of desired mutations.

"Genetic algorithms" are processes which mimic evolutionary processes. Genetic algorithms (GAs) are used in a wide variety of fields to solve problems which are not fully characterized or too complex to allow full characterization, but for which some analytical evaluation is available. That is, GAs are used to solve problems which can be evaluated by some quantifiable measure for the relative value of a solution (or at least the relative value of one potential solution in comparison to another). In the context of the present disclosure, a genetic algorithm is a process for selecting or manipulating character strings in a computer, typically where the character string corresponds to one or more biological molecules (e.g., polynucleotides, polypeptides, etc.).

"Genetic operators" are user-defined operations, or sets of operations, each including a set of logical instructions for manipulating character strings. Genetic operators are applied to cause changes in populations of individuals in order to find interesting (useful) regions of the search space (populations of individuals with predetermined desired properties) by predetermined means of selection. Predetermined (or partially predetermined) means of selection include computational tools (operators comprising logical steps guided by analysis of information describing libraries of character strings), and physical tools for analysis of physical properties of physical objects, which can be built from matter with the purpose of physically creating a representation of information describing libraries of character strings. In some embodiments, some or all of the logical operations are performed in a digital system. When referring to operations on strings (e.g., recombinations, fragmentations, insertions, deletions, etc.) it will be appreciated that the operation can be performed on the encoded representation of a biological molecule or on the "molecule" prior to encoding so that the encoded representation captures the operation.

"Genome" refers to a solution set comprised of individual molecular variants, such as a polynucleotide or polypeptide. For example, a subset of polypeptide variants can comprise a subset of genomes. In some embodiments, a genome is a set of polynucleotide or polypeptide variants, each represented by a gene or character string.

"Hyperbox" or "hypervolume" are used interchangeably herein to refer to a selected region in the objective space (e.g., sequence space) that includes at least one individual (e.g., a scored bio-molecule or character string representation of the bio-molecule variant). A hypervolume can be generated for each biomolecule variant in the population, such as that based on a distance metric in an n-dimensional objective space.

"Library" or "population" is used interchangeably herein to refer to a collection of at least two different molecules and/or character strings, such as polynucleotide sequences (e.g., genes, nucleic acids, etc.) or encoded products (e.g., polypeptides). A library or population generally includes a large number of different molecules. For example, a library or population typically includes at least about 100 different molecules, at least about 1000 different molecules, and often at least about 10000 or more different molecules.

"Mutation" refers to a difference between a given molecular variant and a reference molecule. For a polynucleotide, the mutations can refer to differences in the nucleotide sequence as compared to a reference polynucleotide, while for a polypeptide, mutations can refer to differences in amino acid sequence as compared to a reference polypeptide. Mutations can be represented by changes in the gene as represented by the character string. The number of positions within the molecular variant sequence that can be subject to mutations can be 1 or more, 2 or more, 3 or more, 5 or more, 10 or more, or or more. The number of possible mutations at each position can be 1 or more, 2 or more, 3 or more, 5 or more, 10 or more, or 20 or more. The mutations can correspond to replacement of amino acids or nucleic acids in the reference sequences by other natural or unnatural amino acids or nucleic acids. In some embodiments, "mutations" refers to changes in real polypeptides and polynucleotides. In some embodiments "mutations" refers to changes in the bits of the character strings that represent the genomes.

"Mutation operator" refers to the level of random mutagenesis that can be turned on or off at some specified rate, a mutation rate ("mutrate") defined by the user. In some embodiments, "mutation operator" refers to a genetic operator that changes a single gene in some random, usually small, way. A typical type of mutation is to randomly choose one of the bits in a gene and change its value. Each bit has a probability of being mutated at some specified rate, a mutation rate ("mutrate") defined by the user. Every progeny set of variants is subjected to a low level of random mutagenesis.

"Niche counting" refers to formulating a distance metric in n-dimensional space, where "n" is the number of objectives, and defining a local hypervolume to count the nearest neighbor number of molecular variants contained in the hypervolume or hyperbox. In some embodiments the distance metric is used to create a hypervolume or hyperbox in which the nearest neighbors of a particular variant are contained. Variants with larger numbers of neighbors are penalized. In some embodiments the distance metric is the Euclidian distance. In some embodiments, other distance metrics, such as the Hamming distance, are used.

"Preferred Mutation Frequency" refers to the desired frequency for each mutation, expressed as a number between 0 and 1.

"Preferred Mutation Frequency Weight" refers to the weight assigned to each preferred mutation frequency. The weighted deviations from the preferred frequencies are then used to penalize the overall fitness by adding the following term to the overall fitness:

$$F_p = -\sum_{j=1}^{j=m} w_j \cdot (f_i - \langle f \rangle_j)^2$$

where $F_p$ is the penalty term, $w_j$ is the penalty weight for mutation j, j is the mutation index, m is the number of mutations, $f_j$ is the observed mutation frequency, and $\langle f \rangle_j$ is the average desired mutation frequency.

"Primary fitness" refers to a fitness determined for each genome based on a fitness function, which is applied by a primary fitness operator. In the present disclosure, the primary fitness function is designed to maximize the diversity of the newly generated genomes. The primary fitness can be based on niche counting of hypervolumes or information-maximizing algorithms, such as D-optimality and A-optimality. In some embodiments "Primary Fitness" refers to the main fitness term used to calculate the degree of optimality, independent of other constraints and preferences. The main fitness can be calculated in one of three ways:

D-optimality: $D = |X'X|^{1/m}$ where X is a matrix of variants representing the presence ($x_{ij}=1$) or absence ($x_{ij}=0$) of a given mutation and m is the number of mutations. If more than one mutation is possible at a given position, the matrix is augmented to include an additional column for each additional residue choice available at that position. The elements of such columns would be mutually exclusive since a given position cannot contain more than one mutation choice at a time. For a given row in the matrix, if all elements of a particular column set corresponding to one position are zero, then the backbone is unchanged at that position.

A-optimality: $A = \text{trace } (X'X)^{-1}$.

Niche-count:

$$F = -\sum_{i=1}^{i=n} \frac{1}{nc_i},$$

where $nc_i$ is the niche-count of variant i. The niche-count for each variant is calculated as $$nc_i = \sum_{k=1}^{k=n} c_k,$$

where $$c_k = 1 - \frac{d_{ik}}{\sigma_{share}}$$

for all $d_{ik} < \sigma_{share}$, otherwise $c_k = 0$. The sharing parameter is determined from the transcendental equation $1 + n(\sigma_{share})^m - (1+\sigma_{share})^m = 0$.

"Penalty fitness" refers to a penalty value given for the presence or absence of a given mutation, or sets of mutations, in the genome to drive the results in a particular direction. For example, a penalty function can be associated with the average number of mutations in the population of genomes to restrict the population to a particular number of mutations. The penalty function can be generated for various mutations, such as the absence of a defined mutation associated with a property of the molecule. Additional penalties can come from user preferences that target the average number of mutations per molecular variant and/or the frequency a given mutation should be present within the set of variants. These additional preferences can be weighted with higher or lower penalties, allowing the user to drive the solution in preferred directions.

"Polynucleotide" refers to deoxyribonucleotides or ribonucleotides and polymers (e.g., nucleic acids, etc.) thereof in either single- or double-stranded form, and is used interchangeably herein with "oligonucleotide" and "nucleic acid." Unless specifically limited, the term encompasses nucleic acids containing known analogs of natural nucleotides which have similar binding properties as the reference nucleic acid. Polynucleotides can be polymers of nucleotides, e.g., A, C, T, U, G, etc. or naturally occurring or artificial nucleotide analogues (e.g., peptide nucleic acid, morpholino nucleic acids, etc.), or a character string representing a polymer of nucleotides, depending on context.

"Polypeptide," "protein," "oligopeptide," and "peptide" are used interchangeably to denote a polymer of at least two amino acids covalently linked by an amide bond, regardless of length or post-translational modification (e.g., glycosylation, phosphorylation, lipidation, myristilation, ubiquitination, etc). Included within this definition are D- and L-amino acids, and mixtures of D- and L-amino acids, and amino acid analogues. As used herein, polypeptide also refers to amino acid sequences represented as character strings.

"Repair operator" refers to an operator used to enforce constraints on progeny genomes. In particular, the number nvar of variants to be selected as a plurality of molecular variants is a fixed number, and any genome solution must contain that desired number of bits (variants) be turned on. The repair operator enforces the constraint by randomly turning off (on) bits if there are too many (little) bits to begin with.

In some embodiments "Repair Operator" refers to an operator that is used to enforce constraints on genes. In particular, the number of mutations within a gene can be fixed by the user and any gene must contain no more or less than the defined window of allowable mutations. The repair operator enforces the constraint by randomly turning off (on) bits (corresponding to the presence or absence of a mutation) if there are too many (few) bits to begin with.

"Screening" refers to the process in which one or more properties of one or more bio-molecules are determined. For example, typical screening processes include those in which one or more properties of one or more members of one or more libraries is/are determined. Biomolecules can be screened for thermal stability, solvent stability, activity in performing a chemical reaction, selectivity in performing a chemical reaction, and other properties known in the art.

"Selection" refers to the process in which one or more molecular variants are identified as having one or more properties of interest. Thus, for example, one can screen a library to determine one or more properties of one or more library members. If one or more of the library members is/are identified as possessing a property of interest, it is selected. Selection can refer to physical selection, or in silico selection. In preferred embodiments selection is based on the application of Genetic Algorithms to find molecular variants with preferred properties.

"Selection operator" refers to a tournament selection operator which is used to select a genome from a population of genomes. The first parent is identified by selecting two genomes at random from a population set and the genome with higher fitness is selected for breeding. The other parent is determined in the same fashion.

"Sequence," "gene," and "character strings" are used interchangeably herein to refer to the order and identity of amino acid residues in a protein (i.e., a protein sequence or protein character string) or to the order and identity of nucleotides in a nucleic acid (i.e., a nucleic acid sequence or nucleic acid character string), as encoded by a string of characters or numbers. Any sequence, be it polynucleotide or polypeptide, can be defined by a character string. In some embodiments the variant can be characterized by denoting only the differences between the variant and some reference or wild-type sequence. In some embodiments the character string encodes only the differences (mutations).

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, 1981, *Adv. Appl. Math.* 2:482, by the homology alignment algorithm of Needleman and Wunsch, 1970, *J. Mol. Biol.* 48:443, by the search for similarity method of Pearson and Lipman, 1988, *Proc. Natl. Acad. Sci. USA* 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., *Current Protocols*, Greene Publishing Associates, Inc. and John Wiley & Sons, Inc., (1995 Supplement)). Examples of algorithms that are suitable for determining percent sequence identity and sequence similarity are the BLAST and BLAST 2.0 algorithms, which are described in Altschul et al., 1990, *J. Mol. Biol.* 215: 403-410 and Altschul et al., 1977, *Nucleic Acids Res.* 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, $M=5$, $N=-4$, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, *Proc. Natl. Acad. Sci. USA* 89:10915).

The degree of percent amino acid sequence identity can also be obtained by ClustalW analysis (version W 1.8) by counting the number of identical matches in the alignment and dividing such number of identical matches by the length of the reference sequence, and using the following default ClustalW parameters to achieve slow/accurate pairwise optimal alignments—Gap Open Penalty: 10; Gap Extension Penalty: 0.10; Protein weight matrix: Gonnet series; DNA weight matrix: IUB; Toggle Slow/Fast pairwise alignments=SLOW or FULL Alignment.

Exemplary determination of sequence alignment and % sequence identity can employ the BESTFIT or GAP programs in the GCG Wisconsin Software package (Accelrys, Madison Wis.), using default parameters provided, or the ClustalW multiple alignment program (available from the European Bioinformatics Institute, Cambridge, UK), using, in some embodiments, the parameters above.

6.3 Methods of Creating Optimized Diverse Population of Molecular Variants

The ability to obtain the most information from a limited number of experiments has been the subject of study for many decades (Fisher, R. A., 1935, *The Design of Experiments*, Oliver and Boyd). Generally, the problem is addressed through the use of design of experiments (DOE).

In DOE, mathematical and computational tools are used to maximize the information content while minimizing the number of experimental runs (conditions and measurements). A number of popular approaches based around optimizing various properties of the so called "information matrix" have been used to create experimental designs (Box, E. P., and Draper, N. R., 1987, *Empirical Model Building and Response Surfaces*, Wiley). These approaches are particularly flexible in that they can accommodate constraints on the proposed designs, though such flexibility usually requires additional computational effort in order to find optimized solutions.

In the context of developing a diverse library of polypeptide variants for purposes of screening for improvements or novel properties, the ability to create a set of variants that display maximal phenotypic diversity would be of value. While the use of traditional information content measures, such as D-optimality and A-optimality, (see Box, supra) might prove useful in this regard, maximizing the diversity between the designed polypeptide variants, so as to explore more divergent regions of sequence-function space, yields a somewhat different optimization criterion. In particular, multi-objective evolutionary optimization approaches have made use of the concept of minimizing the count of the nearest neighbors in a high dimensional space to preserve solutions which maximize the population diversity. The approach described herein provides a fast, robust, and advantageous method for creating a set of maximally diverse molecular variants, particularly as the complexity of the problem, such as the number of variants, mutations, and design preferences, grows.

The approach in the present disclosure employs multi-objective optimization procedures, particularly the subfield devoted to evolutionary algorithms (Deb, K., 1999, Multi-objective genetic algorithms: problem difficulties and construction of test problems," *Evolutionary computation* 7, 205-230; incorporated herein by reference). The goal of the methods herein is to create a set of variants that are optimized and maximally diverse. Similar approaches of multi-objective optimization have been shown to work successfully in fields such as software testing, where antirandom tests are written to be as maximally different from each other as possible (Malaiya, Y. K., 1995, "Antirandom testing: getting the most out of black-box testing." *Proceedings of the International Symposium on Software Reliability Engineering*, ISSRE). Additional preferences to target the frequency of specific mutations believed to confer properties of interest (e.g., a penalty function) can be included in the algorithm.

Generally, the number of possible designs resulting from a multi-objective optimization approach is far too large to search exhaustively for the optimal solution. The problem is not reducible to any polynomial time algorithm (Sipser, M., 2005, *Introduction to the Theory of Computation*, 2nd Ed., Course Technology) as the fitness of a solution depends, in general, on the fitnesses of all the other variants present. Thus, multi-objective optimization cannot be done by "hand" or by brute-force methods. Fortunately, evolutionary methods such as genetic algorithms (GAs) are well suited to finding optimized solutions to problems with such extreme combinatorial complexity (Goldberg, D. E., 1989, *Genetic Algorithms in Search, Optimization, and Machine Learning*; incorporated herein by reference).

In view of the foregoing, the present disclosure provides a method for creating an optimized, maximally diverse library of molecular variants, the method comprising the steps of:

(a) inputting a desired set of mutations;
(b) setting optimization parameters, wherein the optimization parameters comprise:
  (i) number nvar of molecular variants to create;
  (ii) molecular variant population size popSize;
  (iii) crossover probability crossrate;
  (iv) mutation rate mutrate;
  (v) repair operator;
  (vi) primary fitness function;
  (vii) penalty fitness function; and
(c) generating a random plurality of genomes of the population size popSize;
(d) creating a first generation of genomes of the size nvar by applying a selection operator, a crossover operator, a mutation operator, a repair operator, a primary fitness operator, and penalty function operator on the plurality of random genomes.

The first generation of genomes, also referred to as a progeny genome, can be evaluated for the desired level of diversity and optimization. In some embodiments, the method comprises repeating step (d) for the first generation of genomes to generate a second generation of genomes for purposes of additional diversity and optimization. Repetition of step (d) for a number of generations nGen can be used to create additional genome subsets. A flow diagram of the method is illustrated in FIG. 1.

In some embodiments the method comprises the steps of:

(a) inputting a desired set of mutations, wherein each mutation has associated with it a preferred frequency of appearance within the set of molecular variants and a weight;
(b) setting optimization parameters, wherein the optimization parameters comprise:
  (i) number nvar of molecular variants to create;
  (ii) molecular variant population size popSize;
  (iii) crossover probability crossrate;
  (iv) mutation rate mutrate;
  (v) repair operator parameters: the minimum, maximum and desired number of mutations per molecular variant;
  (vi) number of generations to evolve nGen;
  (vii) setting the primary fitness function; and
  (viii) setting the penalty fitness functions;
(c) generating a random plurality of sets of molecular variants of the population size popSize, wherein each set of molecular variants is of size nvar; and
(d) evolving new populations of sets of molecular variants for nGen generations by applying a selection operator, a crossover operator, a mutation operator, a repair operator, a primary fitness operator, and penalty function operator, wherein new populations are created by repeating the following steps:|
  (i) selecting sets of molecular variants for breeding based on the selection operator; and
  (ii) breeding sets of molecular variants by;
    (aa) mating the molecular variants using the crossover operator; and
    (bb) mutagenizing progeny sets of molecular variants according to the mutation operator.

The first generation of genomes, also referred to as a progeny genome, can be evaluated for the desired level of diversity and optimization. In some embodiments, the method further comprises repeating step (d) for the first generation of genomes to generate a second generation of genomes for purposes of additional diversity and optimization. Repetition of step (d) for a number of generations nGen can be used to create additional genome subsets.

In some embodiments, the method further comprises the step of synthesizing the final set of molecular variants. In some embodiments, the method further comprises the step of testing the properties of the final set of molecular variants.

The molecules for performing the method can be any molecule where variations can be defined by a descriptor or objective data set, such as a character string. In some embodiments, the molecules comprise bio-molecules, such as polynucleotides or polypeptides. Thus, while many of the embodiments are illustrated for polypeptides, it is to be understood that the present methods can be applied to a variety of systems.

When applied to polypeptides, the desired set of mutations can be chosen for any number of criteria, including but not limited to, frequency of occurrence in a data set, association of the mutation with a particular polypeptide property, and occurrence in a particular region of the polypeptide (for example, a substrate binding pocket). In some embodiments, mutations are associated with changes in one or more polypeptide properties, such as enzyme activity, stereospecificity, stereoselectivity, thermal stability, solvent stability, and inhibitor resistance. All of these properties can serve as objectives and/or constraints on the design of the molecular variants.

Prior to applying the methods of the current invention, the positions along the biomolecule sequence and the possible mutations at these positions are determined. The data set of mutations comprising the desired set of mutations can be obtained from various methods known in the art. Where the mutation data set involve mutations of polypeptide sequences, the data can be obtained from studies of a polypeptide variant library and its associated activities. The polypeptide variant library can be generated from one or more naturally occurring proteins, or engineered recombinant polypeptides. In some embodiments, these can be members encoded by a single gene family, and variants derived from the single gene family. From these seed or starting proteins, the library may be generated by various techniques of mutagenesis, such as by DNA shuffling (Stemmer, 1994, *Proc. Natl. Acad. Sci. USA* 10747-10751; Ness et al., 2002, Nature Biotechnology 20:1251-1255 and U.S. Pat. No. 5,605,793, U.S. Pat. No. 5,811,238, U.S. Pat. No. 5,830,721, U.S. Pat. No. 5,834,252, U.S. Pat. No. 5,837,458, WO/42832, WO 98/27230, WO 99/29902; WO 95/22625; and WO 00/42561; all publications incorporated herein by reference) on nucleic acids encoding part or all of one or more parent proteins. In other embodiments, the polypeptide variant library can be generated by systematically varying the individual residues. Oligonucleotides can be designed to contain the nucleotides required to assemble the diversity present in the degenerate set to generate a population of variants. Variants can be generated in the laboratory or in silico. Details regarding such approaches can be found in, for example, Ness et al. (2002), *Nature Biotechnology* 20:1251-1255, WO 00/42561, WO 00/42560; WO 01/75767, and WO 01/64864. The polynucleotide variant sequences are then transcribed and translated, either in vitro or in vivo, to create a set or library of protein variant sequences.

For each variant in the library or variant population, there are one or more objective data, which describe properties of the molecular variants, as described above. The objective data can include sequence information, which can be characterized in character strings, and/or other properties of the variant, such as activity data. Activity data may be obtained by assays or screens appropriately designed to measure activity magnitudes. Such techniques are well known and are not central to application of the method. For polypeptides with biological activity, e.g., enzymes, the principles for designing appropriate assays or screens are widely understood, and will depend on the type of enzyme, and the desirable properties of the polypeptides. The activity used in the method herein can be protein stability (e.g., thermal or solvent stability), catalytic activity (particularly on structurally different substrates), stereospecificity, stereoselectivity, inhibitor resistance, toxicity, and the like. High throughput assays are particularly suitable for screening polypeptide libraries. For example, each well of a microtiter plate can be used to run a separate assay, or, if concentration or incubation time effects are to be observed, every 5-10 wells can test a single variant (e.g., at different concentrations). Thus, a single standard microtiter plate can assay about 100 (e.g., 96) reactions. It is possible to assay several different plates per day; assay screens for up to about 6,000-20,000 different assays (i.e., involving different nucleic acids, encoded proteins, concentrations, etc.) are possible using the integrated systems. In other embodiments, microfluidic approaches to reagent manipulation have been developed, e.g., by Caliper Technologies (Mountain View, Calif.), which can provide very high throughput microfluidic assay methods. The mutations associated with a particular protein variant characterized by one or more different properties are readily determined from expression libraries by sequencing the polynucleotide encoding the variant polypeptide. In this manner, mutation sets (e.g., one or more amino acid changes) associated with one or more different properties of the polypeptide, can be obtained.

Each mutation has associated with it an input preferred frequency and preferred mutation frequency weight. The frequency refers to the desired frequency for each mutation, expressed as a number between 0 and 1, whereas the mutation frequency weight refers to the weight assigned to each preferred mutation frequency. The weighted deviations from the preferred frequencies are then used to penalize the overall fitness.

Once a data set of mutations is created, a set of optimization parameters is defined, which parameters will operate on the mutation data set for generating a new set of molecular variants having maximal information content, e.g., optimized properties and maximal diversity. The parameters for optimization are as follows:

The first parameter is the number of molecular variants to be created, nvar. This is a finite number set by the user, and constrains the size of the final solution. The value can be set based on any number of criteria, such as the number that can be efficiently screened for the various properties of the molecular variants.

The second parameter is the population size popSize, which is simply the initial starting population of random genomes (number of sets of nvar molecular variants) chosen for processing for fitness and other operations.

The third parameter is the crossover probability rate, crossRate, which is applied to the population by a crossover operator. A crossover operator generally pairs members of the population, and the different parts of the "gene" are cross-combined, resulting in a pair of offspring, i.e., a new pair of possible solutions. A variety of crossover operators that have been developed in the field of genetic algorithms can be used, such as, for example, one point, multipoint, uniform, and arithmetic, each offering different performance (in terms of convergence, or the exploration/exploitation tradeoff) under different conditions. In some embodiments, the crossover event can be set at a fixed rate.

The fourth parameter is the mutation rate mutrate, which is applied to the population by a mutation operator. The mutation operator acts on a member of the population to create, with some defined probability, a change in the character strings of the "gene" (e.g., polypeptide) and acts to maintain diversity within the populations. The crossover operator and mutation operator are used to mate and breed genomes for creating the progeny genome.

The fifth parameter is the fitness function, which comprises at least a primary fitness function, and optionally, one or more penalty fitness functions. The primary fitness is used as part of a selection process to generate a genome subset from a population popSize by selecting out molecular variants that are similar to each other. Variants which are similar to each other are hypothesized to be less likely to display different properties, such as polypeptides with enzymatic activity against substrates not normally recognized by the naturally occurring enzyme. In some embodiments, in order to penalize the fitness of molecular variants which are similar to each other, the concept of a niche counting can be used for determining the primary fitness. Niche counting can comprise formulating a distance metric in an n-dimensional space (where n is the number of positions being mutated). This distance metric, which is essentially the Euclidean distance generalized to n-dimensions, can then be used to define a local hypervolume where the number of nearest neighbors in that space can be counted. Those variants with many neighbors are considered less fit variants as they tend to occupy nearby regions of sequence-function space. The details of formulating the distance metric and niching are described by Deb, supra. The primary fitness function for a candidate solution (set of variants to create) is calculated by summing the inverse of the number of nearby neighbors for every molecular variant in proposed set. Other niche techniques are described in Darwen et al., 1997, "Speciation as automatic categorical modularization," *IEEE Transactions on Evolutionary Computation* 1(2):101-108; Darwen et al., 1996, "Every niching method has its niche: fitness sharing and implicit sharing compared," *Proc. of Parallel Problem Solving from Nature* (PPSN) IV, Vol. 1141, Lecture Notes in Computer Science, pp. 398-407, Springer-Verlag; and Horn et al., 1994, "A niched pareto genetic algorithm for multi-objective optimization," In *Proceedings of the First IEEE Conference on Evolutionary Computation*, IEEE World Congress on Computational Computation, 1:82-87; all publications incorporated herein by reference.

It is to be understood that other types of primary fitness functions can be applied to maximize the diversity of the progeny genome. In some embodiments, the fitness function can be based on D-optimality, A-optimality or other information-based criteria that can be used to construct a matrix of variants containing the maximum information content for an objective data set. As is known in the art, D-optimal designs are straight optimizations based on a chosen optimality criterion and the model that will be fit. The optimality criterion used in generating D-optimal designs is one of maximizing $|X'X|$, the determinant of the information matrix $X'X$. A-optimality is based on the sum of the variances of the estimated parameters for the model, which is the same as the sum of the diagonal elements, or trace, of $(X'X)^{-1}$. Descriptions and applications of D-optimality and A-optimality can be found in Atkinson and Donev, 1992, *Optimal Experimental Designs*, Oxford University Press; Silvey, 1990, *Optimal Design*, Chapman and Hall; Pukelsheim, 1995, *Optimal Design of Experiments*, Chapman and Hall; all publications incorporated herein by reference.

In addition to the primary fitness function, in some embodiments, additional fitness penalties can be ascribed by the user to target other parameters, such as the average number of mutations per variant and/or the frequency a given mutation should be present within the set of variants. These additional penalties can be weighted with higher or lower penalty weights, allowing the user to drive the solution set in preferred directions. For example, the average number of mutations can be restricted to a lower average number of mutations if a higher average number of mutations lead to a significant proportion of the progeny genome being non-active molecules. Similarly, weights given to the frequency of a particular mutation can be adjusted, for example, if a particular mutation adds to the thermal stability of a polypeptide variant independent of other mutations or if a particular amino acid residue is critical to the binding of a ligand and is conserved or invariant when compared to other members of the enzyme family. In the context of polypeptides herein, "evolutionarily conserved" refers to greater than 80% of the polypeptide members having the identical residue at the residue position when the members are aligned by use of a sequence alignment program used to determine percentage sequence identity. An invariant residue refers to a residue that is not changed when all the members are aligned by use of a sequence alignment program.

Although the optimization parameters are described for genetic algorithms, it is to be understood that other strategies may be used in the multi-objective optimization, including, among others, tabu search, simulated annealing, etc.

Upon setting of the optimization parameters, a random plurality of genomes of population size popSize is generated, generally, by a selection operator. This involves picking at random a mutation set and pairing with another mutation set. In some embodiments, the random plurality of genomes of populations size popSize is created by simply picking bits of the character strings at random. To create a new population set from the popSize, i.e., the first generation of genomes or the progeny genomes, the random plurality of genomes is subjected to selection based on genetic operators that include the crossover operator, mutation operator, primary fitness operator, and when present, the penalty fitness operator. These operators function to apply the optimization parameters described above to the random population of genomes. In the present disclosure, the method applies a repair operator to place constraints on the selection by limiting the size of the progeny genome to a user-defined, finite number nvar. If the progeny genome size is less than nvar, the repair operator enforces the constraint by turning bits on to generate additional molecular variants to satisfy nvar. If the progeny population greater than nvar, the repair operator enforces the constraint by turning bits off to reduce the number of molecular variants to satisfy nvar. In some embodiments, the repair operator is used to enforce constraints on genes. In particular, the minimum and maximum number of mutations within a gene can be fixed by the user. The repair operator assures that the number of mutations in any gene falls within this defined window. The repair operator enforces this constraint by randomly turning on or off bits in the gene's character string, which correspond to the presence or absence of a mutation, to maintain a desired number of mutations.

Thus, in some embodiments, the invention relates to a set of molecular variants, particularly polypeptide variants, generated by the methods described herein. In some embodiments, the set of optimally diverse molecular variants are generated by a method of:

(a) inputting a desired set of mutations;
(b) setting optimization parameters, wherein the optimization parameters comprise:
  (i) number nvar of molecular variants to create;
  (ii) molecular variant population size popSize;
  (iii) crossover probability crossrate;
  (iv) mutation rate mutrate;
  (v) repair operator;
  (vi) primary fitness function; and
  (vii) penalty fitness function;
(c) generating a random plurality of genomes of the population size popSize; and
(d) creating a first generation of genomes of the size nvar by applying a selection operator, a crossover operator, a mutation operator, a repair operator, a primary fitness operator, and penalty function operator on the plurality of random genomes.

Once the optimized, diverse set of molecular variants is determined, the molecular variants are synthesized. The synthesis of the variants can be accomplished by any of the means commonly used in the art, and includes the use of automated synthesis techniques. In some embodiments, the method creates the instructions needed to control an automated synthesis machine.

In some embodiments, the set of optimally diverse molecular variants is made by the method of:
(a) inputting a desired set of mutations, wherein each mutation has associated with it a preferred frequency of appearance within the set of molecular variants and a weight;
(b) setting optimization parameters, wherein the optimization parameters comprise:
  (i) number nvar of molecular variants to create;
  (ii) molecular variant population size popSize;
  (iii) crossover probability crossrate;
  (iv) mutation rate mutrate;
  (v) repair operator parameters: the minimum, maximum and desired number of mutations per variant;
  (vi) number of generations to evolve nGen;
  (vii) setting the primary fitness function; and
  (viii) setting the penalty fitness functions;
(c) generating a random plurality of sets of molecular variants of the population size popSize, wherein each set of molecular variants is of size nvar; and
(d) evolving new populations of sets of molecular variants for nGen generations by applying a selection operator, a crossover operator, a mutation operator, a repair operator, a primary fitness operator, and penalty function operator, wherein new populations of molecular variants are created by repeating the following steps:|
  (i) selecting sets of molecular variants for breeding based on the selection operator; and
  (ii) breeding sets of molecular variants by;
    (aa) mating the molecular variants using the crossover operator; and
    (bb) mutagenizing progeny sets of molecular variants according to the mutation operator.

In some embodiments, the creation of the molecular variants further comprises the step of synthesizing the final set of molecular variants. In some embodiments, the creation of the molecular variants further comprises the step of testing the properties of the final set of molecular variants.

For purposes of illustration, a progeny genome of polypeptides can be generated by recombinant techniques, and each variant expressed in an appropriate expression system, either in vitro or in vivo. The progeny genome resulting from application of the optimization parameters and corresponding operators is experimentally evaluated for the desired properties, as well as diversity. The synthesized polypeptides are evaluated for the desired properties, such as activity, stability and other profiles. If it is desirable to obtain additional optimization and diversification, the process of creating progeny genomes can be reiterated to generate a second generation of genomes. Continued reiteration for a number of generations nGen allows evaluation of a number of different solutions sets for optimization and diversity of properties.

The methods herein can be used alone or in conjunction with other methods, such as methods of selecting an optimized diverse population of molecules. For example, the set of variants can be selected by various optimization procedures designed for selection of one or a plurality of molecular variants, such as those described in US application publications 20040072245, 20060195204, 20060205003, and 20070208677, all of which are incorporated herein by reference. A set of variants having defined mutations can then be tapped for mutation data, and used for creating additional molecular variants for further optimization and diversity.

6.4 Computer Implementation and Systems

The present disclosure further provides the method above in the form of computer software to implement the method in a computer. Generally, the computer program product comprises a machine readable storage medium having program instructions comprising:
(a) code for receiving a data set of mutations;
(b) code for setting optimization parameters, wherein the optimization parameters comprise
  (i) number nvar of molecular variants to create;
  (ii) molecular variant population size popSize;
  (iii) crossover rate crossrate;
  (iv) mutation rate mutrate;
  (vi) primary fitness function;
  (vii) penalty fitness function; and
(c) code for generating a random plurality of genomes of the population size popSize;
(d) code for creating a first optimized genomes from the random plurality of genome by applying a selection operator; a crossover operator; a mutation operator; a primary fitness operator; a penalty fitness operator; and a repair operator.

In some embodiments, the computer program can comprise a computer code for applying a fitness function selected from niche counting, D-optimality or A-optimality. In addition, the computer program can further comprise a computer code for applying a penalty fitness function, such as penalties for the average number of mutations per genome, and penalties for presence or absence of defined mutation sets.

The computer program can further comprise a code for reiteratively performing step (d) for nGen number of generations on the first generation of genomes to generate additional generations of optimized diverse genomes.

The computer program can further comprise a code for displaying information about the completed selection of molecule variants on an output device. This information includes the mutations determined for each molecular variant, the frequencies of each mutation, and the information content of the set of molecular variants. In some embodiments, the computer program further comprises a code to create the set of instructions needed to control the automated synthesis of the molecular variants. In some embodiments the computer program controls a synthesis robot in order to synthesize the set of molecular variants. In some embodiments, computer program further comprises a code to communicate to a commercial synthesize company a set of synthesis instructions or an order. In some embodiments, computer program can further comprise a code to transmit the synthesis instructions or order over the internet.

In some embodiments the computer program product comprises a machine readable storage medium having program instructions comprising:

(a) code for inputting a desired set of mutations, wherein each mutation has associated with it a preferred frequency of appearance within the set of molecular variants and a weight;

(b) code for setting optimization parameters, wherein the optimization parameters comprise:
(i) number nvar of molecular variants to create;
(ii) molecular variant population size popSize;
(iii) crossover probability crossrate;
(iv) mutation rate mutrate;
(v) repair operator parameters: the minimum, maximum and desired number of mutations per molecular variant;
(vi) number of generations to evolve nGen;
(vii) setting the primary fitness function; and
(viii) setting penalty fitness functions;

(c) code for generating a random plurality of sets of molecular variants of the population size popSize, wherein each set of molecular variants is of size nvar; and (d) code for evolving new populations of sets of molecular variants for nGen generations by applying a selection operator, a crossover operator, a mutation operator, a repair operator, a primary fitness operator, and penalty function operator. The code creates these new populations by repeating the following steps:|
(i) selecting sets of molecular variants for breeding based on the selection operator; and
(ii) breeding sets of molecular variants by;
(aa) mating the molecular variants using the crossover operator; and
(bb) mutagenizing progeny sets of molecular variants according to the mutation operator.

In some embodiments the computer program product further comprises code for creating the instructions needed to synthesize the final set of molecular variants. In some embodiments the computer program product further comprises code for displaying the final results on an output device.

The computer-readable storage medium can be any storage medium, such as, for example, semiconductor memory devices (e.g., ROM), CD-ROM, memory key, flash memory card, diskette, magnetic tape, having stored thereon a program which, when executed in a computing environment, provides for implementation of algorithms to carry out all or a portion of the methods above. Where the computer-readable medium contains a complete program for carrying out the methods described herein, the program includes program instructions for collecting, analyzing and generating output, and generally includes computer readable code devices for interacting with a user as described herein, and processing the input data. In addition, embodiments of the computer-implemented method also relate to computer readable media or computer program products that include program instructions and/or data (including data structures) for delivering and performing various computer implemented operations. Examples of program instructions include both low-level code, such as produced by a compiler, and files containing higher level code that may be executed by the computer using an interpreter. Further, the program instructions include machine code, source code and any other code that directly or indirectly controls operation of a computing machine in accordance with the descriptions herein. The code may specify the input, output, calculations, conditionals, branches, iterative loops, etc.

In various embodiments, standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Paradox™) can be adapted to the embodiments herein by inputting one or more character strings into the software which is loaded into the memory of a digital system, and performing an operation as noted herein on the character string. For example, systems can include the foregoing software having the appropriate character string information, e.g., used in conjunction with a user interface (e.g., a GUI in a standard operating system such as a Windows, Macintosh or LINUX system) to manipulate strings of characters.

Further provided here are systems for generating an optimized diverse population of genomes, comprising:

(a) at least one computer comprising a database capable of storing a data set representing a plurality of mutations;

(b) a system software comprising one or more logic instructions for
(i) selecting a random plurality of parental mutations to generate a plurality of genomes of size popSize; and
(c) creating a first generation of genome (i.e., a progeny genome) by applying to the random population a crossover operator, a mutation operator, a primary fitness operator, a penalty fitness operator, and a repair operations.

The logic instructions for the primary fitness and penalty fitness operators can comprise the various forms of the fitness functions described herein.

In some embodiments, the invention further provides a system for generating an optimized diverse population of molecular variants, the system comprising:

(a) at least one computer comprising a database capable of storing a data set of mutations, wherein each mutation has associated with it a preferred frequency of appearance within the set of molecular variants and a weight;

(b) system software comprising one or more logic instructions for setting optimization parameters, wherein the optimization parameters comprise:
(i) number nvar of molecular variants to create;
(ii) molecular variant population size popSize;
(iii) crossover probability crossrate;
(iv) mutation rate mutrate;
(v) repair operator parameters: the minimum, maximum and desired number of mutations per molecular variant;
(vi) number of generations to evolve nGen;
(vii) setting the primary fitness function; and
(viii) setting penalty fitness functions;

(c) system software comprising one or more logic instructions for generating a random plurality of sets of molecular variants of the population size popSize; and (d) system software comprising one or more logic instructions for evolving new populations of sets of molecular variants of the size nvar for nGen generations by applying a selection operator, a crossover operator, a mutation operator, a repair operator, a primary fitness operator, and penalty function operator, wherein new populations are created by repeating the steps of:
(i) selecting sets of molecular variants for breeding based on the selection operator; and (ii). breeding sets of molecular variants by;
  (aa) mating the molecular variants using the crossover operator; and
  (bb) mutagenizing progeny sets of molecular variants according to the mutation operator.

In some embodiments the system further comprises one or more logic instructions for creating synthesis instructions for the final set of molecular variants. In some embodiments the system further comprises system software comprising one or more logic instructions for displaying the output data on at least one output device.

In various embodiments, the computer of the systems typically include, e.g., a digital computer with the software for performing the various steps of the method. The computer can be, e.g., a PC (Intel x86 or Pentium chip-compatible DOS™, OS2™, WINDOWS™, WINDOWS95™, WINDOWS98™, LINUX, Apple-compatible, MACINTOSH™ compatible, Power PC compatible, or a UNIX compatible (e.g., SUN™ work station or machine) or other common commercially-available computers known in the art. The software for carrying out the steps can be constructed by one of skill using a standard programming language such as Visual Basic, FORTRAN, Basic, Java, or the like, according to the methods herein. Any controller or computer optionally includes a monitor which can include, e.g., a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard, touch screen, or mouse optionally provide for input from a user and for user selection of mutations or setting of optimization parameters. Display devices provide a means of monitoring of the creation of the molecular variants as well as providing details of the set of molecular variants created. These details include the mutations determined for each molecular variant, the frequencies of each mutation, and the information content of the set of molecular variants.

The computer also includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the system to carry out any desired operations. The digital system can also include output elements for displaying the results of the method.

Thus, in some embodiments, the computer implemented method for generating an optimally diverse population of molecular variants can comprise
(a) inputting and storing a desired set of mutations in a first computer memory;
(b) inputting and storing optimization parameters in a second computer memory, wherein the optimization parameters comprise:
  (i) number nvar of molecular variants to create;
  (ii) molecular variant population size popSize;
  (iii) crossover probability crossrate;
  (iv) mutation rate mutrate;
  (v) repair operator;
  (vi) primary fitness function; and
  (vii) penalty fitness function;
(c) retrieving and processing the input of (a) with a computer microprocessor, wherein the microprocessor applies a computer program that generates a random plurality of genomes of the population size popSize; and
(d) retrieving the input (b) and applying a computer program for a selection operator, a crossover operator, a mutation operator, a repair operator, a primary fitness operator, and penalty function operator on the plurality of random genomes of population size popSize of (c) using the computer microprocessor, thereby creating a first generation of genomes of the size nvar. In some embodiments, the method can further comprise outputting the genomes to a display device, such as a printer or monitor.

In some embodiments, the computer implemented method of generating a set of optimally diverse set of molecular variants can comprise:
(a) inputting and storing a desired set of mutations in a first computer memory, wherein each mutation has associated with it a preferred frequency of appearance within the set of molecular variants and a weight;
(b) inputting and storing optimization parameters in a second computer memory, wherein the optimization parameters comprise:
  (i) number nvar of molecular variants to create;
  (ii) molecular variant population size popSize;
  (iii) crossover probability crossrate;
  (iv) mutation rate mutrate;
  (v) repair operator parameters: the minimum, maximum and desired number of mutations per molecular variant;
  (vi) number of generations to evolve nGen;
  (vi) setting the primary fitness function; and
  (vii) setting the penalty fitness functions;
(c) retrieving and processing the input of (a) with a computer microprocessor, wherein the microprocessor applies a computer program for generating a random plurality of sets of molecular variants of the population size popSize, wherein each set of molecular variants is of size nvar; and
(d) retrieving the input of (b) and applying a computer program for a selection operator, a crossover operator, a mutation operator, a repair operator, a primary fitness operator, and penalty function operator using the computer microprocessor to generate new populations of sets of molecular variants for nGen generations, wherein additional populations of molecular variants are created by repeating the following steps:|
  (i) selecting sets of molecular variants for breeding based on the selection operator; and
  (ii) applying a computer program for breeding sets of molecular variants;
    (aa) mating the molecular variants using the crossover operator; and
    (bb) mutagenizing progeny sets of molecular variants according to the mutation operator.

In some embodiments, the method can further comprise applying a computer program to create instructions for the synthesizing the final set of molecular variants. In some embodiments, the method can further comprise using a computer program to control a synthesis robot. In some embodiments, the method can further comprise using a computer program to output the final set of molecular variants to a display device, such as a printer or monitor.

4.5 Implementation Via the Internet

In some embodiments, the method herein can be implemented via the internet. The internet includes computers, information appliances, and computer networks that are interconnected through communication links. The interconnected computers exchange information using various services, such as electronic mail, ftp, the World Wide Web ("WWW") and other services, including secure services. The WWW service can be understood as allowing a server computer system (e.g., a Web server or a Web site) to send web pages of information to a remote client information appliance or computer system. The remote client computer system can then display the web pages. Generally, each resource (e.g., computer or web page) of the WWW is uniquely identifiable by a Uniform Resource Locator ("URL"). To view or interact with a specific web page, a client computer system specifies a URL for that web page in a request. The request is forwarded to a server that supports that web page. When the server receives the request, it sends that web page to the client information system. When the client computer system receives that web page, it can display the web page using a browser or can interact with the web page or interface as otherwise provided. A browser is a logic module that effects the requesting of web pages and displaying or interacting with web pages. Currently, displayable web pages are typically defined using a Hyper Text Markup Language ("HTML"). HTML provides a standard set of tags that define how a web page is to be displayed. An HTML document contains various tags that control the displaying of text, graphics, controls, and other features. The HTML document may contain URLs of other Web pages available on that server computer system or other server computer systems. URLs can also indicate other types of interfaces, including such things as CGI scripts or executable interfaces that information appliances use to communicate with remote information appliances or servers without necessarily displaying information to a user. In some embodiments communication over the internet is done using a wired (for example, Ethernet) network. In some embodiments communication over the internet is done using a wireless (for example, WIFI) network The internet is especially conducive to providing information services to one or more remote users or customers. In some embodiments, the methods herein can be implemented via a client-server model or system, where the server provides a user interface and the logic instructions for carrying out one or more of the various steps of the method. The server can provide an interface for entry of a list of desired mutations and entry of any user definable parameters including, but not limited to, the size of genomes to be selected (i.e., nvar), the population of the random genomes popSize and the various optimization parameters, including, crossover rate crossrate; the mutation rate mutrate; the type of primary fitness function, for example niche counting, D-optimality, and A-optimality; and penalty fitness function. The server also can provide a set of default values optimal under the conditions of carrying out the method of selecting the set of molecular variants. The user or client may access the interface using a web browser and allow selection of the various user definable parameters. When the user has completed selecting the items desired, the server computer system may then prompt the user for any other information needed to complete the service. The server then completes the operations needed to create the set of molecular variants. The server displays information about the completed selection back to the client computer. This information includes the mutations determined for each molecular variant, the frequencies of each mutation, and the information content of the set of molecular variants. In some embodiments, the information needed to synthesize the molecular variants is in the form of instructions that control a synthesis robot. In some embodiments the server controls a synthesis robot in order to synthesize the set of molecular variants. In some embodiments, the information needed to synthesize the molecular variants is communicated to a commercial synthesize company in the form of synthesis instructions or an order. In some embodiments, the order is transmitted over the internet. This transaction-specific order information may include the purchaser's name or other identification, an identification for payment (such as a corporate purchase order number or account number), or additional information needed to complete the service. Upon entry of necessary information by the client through the interface, the server provides the logic instructions for applying the method based on the parameters set by the user. The results can be displayed as a web page, such as in the form of a HTML document.

In some embodiments the invention provides a network-based method of creating a diverse optimized set of molecular variants, the method comprising the steps of:

(a) obtaining, at the server from the network, a desired list of mutations and values of optimization parameters entered at a client device; wherein each mutation has associated with it a preferred frequency of appearance within the set of molecular variants and a weight; and wherein the optimization parameters comprise:

(i) number nvar of molecular variants to create;
(ii) molecular variant population size popSize;
(iii) crossover probability crossrate;
(iv) mutation rate mutrate;
(v) repair operator parameters: the minimum, maximum and desired number of mutations per molecular variant;
(vi) number of generations to evolve nGen;
(vii) setting the primary fitness function; and
(viii) setting penalty fitness functions;

(b) generating, at the server, a random plurality of sets of molecular variants of the population size popSize; and (c) evolving new populations of sets of molecular variants of the size nvar for nGen generations by applying, at the server, a selection operator, a crossover operator, a mutation operator, a repair operator, a primary fitness operator, and penalty function operator, wherein new populations are created at the server by repeating the steps of:

(i) selecting sets of molecular variants for breeding based on the selection operator; and
(ii). breeding sets of molecular variants by;
   (aa) mating the molecular variants using the crossover operator; and
   (bb) mutagenizing progeny sets of molecular variants according to the mutation operator.

In some embodiments the network-based method further comprises the step creating, at the server, synthesis instructions for the final set of molecular variants. In some embodiments the network-based method further comprises the step displaying the output data on the client device.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

The following Example is set forth to aid in the understanding of the invention, and is not intended and should not be construed to limit in any way the invention set forth in the claims which follow thereafter.

5. EXAMPLE

Example 1

Creating a Hypothetical Set of Molecular Variants

The following example shows how a defined set of 13 mutations are applied to a reference or wild-type sequence, in order to produce a set of 90 molecular variants, which would be synthesized and screened for improved properties.

The set of 13 mutations were defined as: V90I, N93D, A118E, C118L, Y181F, I194V, T214V, N214I, G228N, V245I, S276E, K277Q, N299D, where the first letter refers to the single letter amino acid code of the amino acid present in the reference sequence, the number refers to the position of the amino acid within the reference sequence, and the final letter refers to the single letter amino acid code for the mutation. The following preferences and parameters were used for optimization:

TABLE 1

The input mutations, their frequency preferences, and their weights. For each mutation, the desired frequency and weight are given. For example, for 90I, the desired frequency is that 31% of all variants should contain this mutation and the weight for this preference is 50.

| Mutation | Frequency | Weight |
|---|---|---|
| 90I | 0.31 | 50 |
| 93D | 0.31 | 50 |
| 118E | 0.31 | 50 |
| 118L | 0.31 | 50 |
| 181F | 0.31 | 50 |
| 194V | 0.31 | 50 |
| 214V | 0.31 | 50 |
| 214I | 0.31 | 50 |
| 228N | 0.31 | 50 |
| 245I | 0.31 | 50 |
| 276E | 0.31 | 50 |
| 277Q | 0.31 | 50 |
| 299D | 0.31 | 50 |

No specific variant was required to be produced. The number of molecular variants to create was set at 90. The average number of mutations per molecular variant was set at 4 with a hard minimum of 3 and a hard maximum of 5. The weight for this average preference of 4 was set at 0.1.

The number of generations to evolve was 100. The crossover rate was 2. The mutation rate was 1%. The population size was 100. The primary fitness objective was to maximize D-optimality. After 100 generations the software generated the following set of variants:

TABLE 2

Amino Acid Mutations. Each row of the table represents a molecular variant, having from 3 to 5 mutations.
Amino Acid Mutations

| | | | | |
|---|---|---|---|---|
| A118E | I194V | V245I | S276E | |
| A118L | Y181F | T214I | G228N | |
| Y181F | I194V | T214I | G228N | S276E |
| V90I | A118L | Y181F | N299D | |
| N93D | Y181F | T214I | V245I | N299D |
| V90I | N93D | A118E | Y181F | T214I |
| A118E | Y181F | T214V | V245I | |
| V90I | A118L | Y181F | T214I | |

TABLE 2-continued

Amino Acid Mutations. Each row of the table represents a molecular variant, having from 3 to 5 mutations.
Amino Acid Mutations

| | | | | |
|---|---|---|---|---|
| Y181F | I194V | S276E | N299D | |
| N93D | A118L | T214V | N299D | |
| V90I | N93D | G228N | V245I | S276E |
| V90I | A118E | T214V | V245I | |
| Y181F | T214V | G228N | V245I | |
| V90I | Y181F | T214I | S276E | K277Q |
| Y181F | I194V | T214V | K277Q | |
| N93D | A118E | T214I | | |
| V90I | I194V | T214I | G228N | K277Q |
| I194V | T214I | G228N | V245I | S276E |
| V90I | A118E | T214I | G228N | |
| Y181F | I194V | G228N | N299D | |
| V90I | N93D | T214I | V245I | N299D |
| Y181F | T214V | V245I | | |
| A118L | T214V | G228N | S276E | |
| V90I | A118E | Y181F | I194V | |
| N93D | A118E | I194V | K277Q | |
| V90I | I194V | K277Q | N299D | |
| V90I | A118E | S276E | K277Q | |
| V90I | A118L | T214V | G228N | V245I |
| N93D | A118E | T214I | V245I | N299D |
| N93D | A118L | I194V | T214I | |
| N93D | T214I | S276E | | |
| V90I | A118L | I194V | T214I | |
| V90I | N93D | T214I | K277Q | |
| V90I | A118L | I194V | V245I | N299D |
| V90I | G228N | V245I | K277Q | N299D |
| A118L | G228N | V245I | S276E | |
| V90I | N93D | A118E | G228N | N299D |
| A118E | T214I | S276E | N299D | |
| N93D | Y181F | G228N | V245I | |
| N93D | I194V | T214V | V245I | S276E |
| V90I | Y181F | V245I | K277Q | |
| N93D | Y181F | I194V | K277Q | N299D |
| T214I | G228N | S276E | N299D | |
| N93D | A118E | Y181F | G228N | K277Q |
| A118L | T214V | K277Q | N299D | |
| N93D | I194V | T214V | S276E | |
| N93D | A118L | S276E | K277Q | |
| N93D | A118E | I194V | V245I | |
| N93D | A118L | T214V | K277Q | |
| N93D | A118L | G228N | | |
| A118L | Y181F | S276E | | |
| A118L | G228N | V245I | S276E | N299D |
| T214I | V245I | K277Q | | |
| A118L | T214V | V245I | N299D | |
| N93D | Y181F | V245I | K277Q | N299D |
| T214V | G228N | K277Q | | |
| N93D | T214V | G228N | S276E | N299D |
| N93D | A118L | T214I | N299D | |
| A118E | T214V | S276E | N299D | |
| A118L | T214I | K277Q | N299D | |
| V90I | Y181F | T214V | S276E | N299D |
| V90I | I194V | T214V | N299D | |
| A118E | T214I | G228N | | |
| A118L | I194V | T214I | V245I | |
| I194V | T214V | K277Q | | |
| A118E | V245I | S276E | K277Q | |
| A118E | T214V | G228N | S276E | |
| V90I | N93D | A118L | Y181F | |
| V90I | N93D | G228N | K277Q | N299D |
| A118L | Y181F | I194V | S276E | |
| V90I | A118E | I194V | G228N | |
| A118E | T214I | G228N | K277Q | |
| A118E | Y181F | T214I | G228N | N299D |
| V90I | A118E | T214V | V245I | |
| A118E | Y181F | I194V | K277Q | |
| N93D | A118E | Y181F | G228N | |
| V90I | Y181F | T214I | S276E | |
| A118E | I194V | T214I | V245I | |
| G228N | V245I | S276E | K277Q | N299D |
| A118E | S276E | K277Q | | |
| V90I | Y181F | V245I | S276E | |
| A118E | T214I | V245I | K277Q | |
| N93D | I194V | T214V | G228N | K277Q |
| A118E | Y181F | I194V | V245I | N299D |

TABLE 2-continued

Amino Acid Mutations. Each row of the table represents a molecular variant, having from 3 to 5 mutations.
Amino Acid Mutations

| | | | | |
|---|---|---|---|---|
| I194V | T214I | K277Q | N299D | |
| V90I | A118L | Y181F | G228N | K277Q |
| V90I | N93D | I194V | T214V | G228N |
| A118L | I194V | G228N | N299D | |
| Y181F | T214V | G228N | V245I | K277Q |
| N93D | G228N | S276E | K277Q | |

TABLE 3

Desired mutations and their resulting mutation counts. For each mutation, the integer represents the number of times that mutation is programmed within the set of 90 variants.

| Mutation | Number of Occurrences |
|---|---|
| 90I | 29 |
| 93D | 30 |
| 118E | 27 |
| 118L | 25 |
| 181F | 31 |
| 194V | 29 |
| 214V | 24 |
| 214I | 29 |
| 228N | 34 |
| 245I | 31 |
| 276E | 28 |
| 277Q | 31 |
| 299D | 30 |

The average incorporation rate is 32.3%, standard deviation=2.7%, range [26.6%, 37.7%], consistent with the desired average rate of 31%. The number of molecular variants having 3 mutations was 10, 4 mutations was 52, and 5 mutations was 28, with an average of 4.2 mutations, consistent with the hard limits of 3 to 5 and desired average mutation rate of 4.

The D-optimal score was 86.16, where $D=|X'X|^{(1/13)}$ and X is the mutation matrix containing entries of 0 or 1 indicating the absence (0) or presence (1) of a given mutation.

The list of molecular variants given above can be created by any number of commercially available gene synthesis providers.

What is claimed is:

1. A set of physical bio-molecules produced by a method comprising:
   (a) inputting a desired set of mutations;
   (b) setting optimization parameters, wherein the optimization parameters comprise:
       (i) number nvar of molecular variants to create;
       (ii) molecular population size popSize;
       (iii) a crossover rate;
       (iv) a mutation rate;
       (v) repair operator;
       (vi) a primary fitness function; and
       (vii) a penalty fitness function;
   (c) generating a plurality of random genomes of population size popSize;
   (d) creating a diverse, optimized set of molecular variants of the size nvar by applying a selection operator; a crossover operator; a mutation operator; a repair operator; a primary fitness function operator; and penalty function operator on the plurality of random genomes, wherein operations (a)-(d) are performed by executing instructions on a computer system programmed to perform said operations, and wherein each molecular variant represents a bio-molecule sequence; and
   (e) synthesizing or expressing, in vitro or in vivo, a set of physical bio-molecules, wherein each physical bio-molecule comprises or is encoded by a polymer having a bio-molecule sequence represented by a molecular variant of the diverse, optimized set of molecular variants.

2. The set of physical bio-molecules of claim 1, wherein the primary fitness function is based on niche counting.

3. The set of physical bio-molecules of claim 1, wherein the penalty fitness function is the average number of mutations per genome.

4. The set of physical bio-molecules of claim 1, wherein the penalty fitness function is an occurrence of a defined mutation in a genome, and wherein the defined mutation is a mutation that increases thermal stability of polypeptide variants.

5. The set of physical bio-molecules of claim 1, wherein the penalty fitness function is an occurrence of a defined mutation in a genome, and wherein the defined mutation is an evolutionarily invariant residue.

6. The set of physical bio-molecules of claim 1, wherein the primary fitness function is based on D-optimality or A-optimality.

7. The set of physical bio-molecules of claim 1, wherein the penalty fitness function is an occurrence of a defined mutation in a genome, and wherein the defined mutation is a mutation that increases substrate recognition.

8. The set of physical bio-molecules of claim 1, wherein the bio-molecules comprises a molecule selected from the group consisting of: a polynucleotide, a polypeptide, a lipid, a carbohydrate, and any combinations thereof.

9. A set of physical bio-molecules produced by a method comprising the steps of:
   (a) inputting a desired set of mutations, wherein each mutation has associated with it a preferred frequency of appearance within a set of molecular variants and a weight;
   (b) setting optimization parameters, wherein the optimization parameters comprise:
       (i) number nvar of molecular variants to create;
       (ii) molecular variant population size popSize;
       (iii) crossover probability crossrate;
       (iv) mutation rate mutrate;
       (v) repair operator parameters: the minimum, maximum and desired number of mutations per molecular variant;
       (vi) number of generations to evolve nGen;
       (vii) a primary fitness function; and
       (viii) a penalty fitness function;
   (c) generating a random plurality of sets of molecular variants of the population size popSize; and
   (d) evolving random pluralities of sets of molecular variants of the size nvar for nGen generations by applying a selection operator, a crossover operator, a mutation operator, a repair operator, a primary fitness operator, and penalty function operator, wherein a diverse, optimized set of molecular variants are created by repeating the steps of:
       (i) selecting sets of molecular variants for breeding based on the selection operator;
       (ii) breeding sets of molecular variants;
           (aa) mating the molecular variants using the crossover operator;
           (bb) mutagenizing progeny sets of molecular variants according to the mutation operator,
wherein operations (a)-(d) are performed by executing instructions on a computer system programmed to perform said operations, and wherein each molecular variant represents a bio-molecule sequence; and (e) synthesizing or expressing, in vitro or in vivo, a set of physical bio-molecules, wherein each physical bio-molecule comprises or is encoded by a polymer having a bio-molecule sequence represented by a molecular variant of the diverse, optimized set of molecular variants.

10. The set of physical bio-molecules of claim 9, wherein the primary fitness function is based on niche counting.

11. The set of physical bio-molecules of claim 9, wherein the penalty fitness function is the average number of mutations per genome.

12. The set of physical bio-molecules of claim 9, wherein the penalty fitness function is an occurrence of a defined mutation in a genome, and wherein the defined mutation is a mutation that increases thermal stability the molecular variants.

13. The set of physical bio-molecules of claim 9, wherein the penalty fitness function is an occurrence of a defined mutation in a genome, and wherein the defined mutation is an evolutionarily invariant residue.

14. The set of physical bio-molecules of claim 9, wherein the method further comprises testing the properties of the set of physical bio-molecules.

15. The set of physical bio-molecules of claim 9, wherein the primary fitness function is based on D-optimality or A-optimality.

16. A method comprising:
    (a) inputting a desired set of mutations;
    (b) setting optimization parameters, wherein the optimization parameters comprise:
        (i) number nvar of molecular variants to create;
        (ii) molecular population size popSize;
        (iii) a crossover rate;
        (iv) a mutation rate;
        (v) repair operator;
        (vi) a primary fitness function; and
        (vii) a penalty fitness function;
    (c) generating a plurality of random genomes of population size popSize;
    (d) creating a diverse, optimized set of molecular variants of the size nvar by applying a selection operator; a crossover operator; a mutation operator; a repair operator; a primary fitness function operator; and penalty function operator on the plurality of random genomes, wherein operations (a)-(d) are performed by executing instructions on a computer system programmed to perform said operations, and wherein each molecular variant represents a bio-molecule sequence; and
    (e) synthesizing or expressing, in vitro or in vivo, a set of physical bio-molecules, wherein each physical bio-molecule comprises or is encoded by a polymer having a bio-molecule sequence represented by a molecular variant of the diverse, optimized set of molecular variants.

17. The set of physical bio-molecules of claim 16, wherein the penalty fitness function is an occurrence of a defined mutation in a genome, and wherein the defined mutation is a mutation that increases substrate recognition.

18. The method of claim 16, wherein the primary fitness function is based on niche counting.

19. The method of claim 16, wherein the primary fitness function is based on D-optimality or A-optimality.

20. The method of claim 16, wherein the penalty fitness function is the average number of mutations per genome.

21. The method of claim 16, wherein the penalty fitness function is an occurrence of a defined mutation in a genome, and wherein the defined mutation is a mutation that increases thermal stability of polypeptide variants.

22. The set of physical bio-molecules of claim 16, wherein the penalty fitness function is an occurrence of a defined mutation in a genome, and wherein the defined mutation is a mutation that increases substrate recognition.

23. The set of physical bio-molecules of claim 16, wherein the penalty fitness function is an occurrence of a defined mutation in a genome, and wherein the defined mutation is a mutation that increases substrate recognition.

* * * * *